(12) United States Patent
Zhao

(10) Patent No.: US 8,084,506 B2
(45) Date of Patent: Dec. 27, 2011

(54) SEBUM ABSORPTION COMPOSITIONS

(75) Inventor: Wanli Zhao, Dallas, TX (US)

(73) Assignee: Mary Kay Inc., Dallas, TX (US)

( * ) Notice: Subject to any disclaimer, the term of this patent is extended or adjusted under 35 U.S.C. 154(b) by 378 days.

(21) Appl. No.: 12/408,182

(22) Filed: Mar. 20, 2009

(65) Prior Publication Data

US 2009/0247648 A1 Oct. 1, 2009

Related U.S. Application Data

(60) Provisional application No. 61/039,337, filed on Mar. 25, 2008.

(51) Int. Cl.
*A61K 47/24* (2006.01)
(52) U.S. Cl. ...................................... 514/772
(58) Field of Classification Search .................. 514/772
See application file for complete search history.

(56) References Cited

U.S. PATENT DOCUMENTS

| | | | |
|---|---|---|---|
| 3,439,088 A | 4/1969 | Edman | 424/63 |
| 3,818,105 A | 6/1974 | Coopersmith et al. | 514/789 |
| 6,200,964 B1 | 3/2001 | Singleton et al. | 514/159 |
| 6,346,238 B1 | 2/2002 | Ascione et al. | 424/65 |
| 6,444,212 B1 | 9/2002 | Cavazzuti et al. | 424/401 |
| 6,645,502 B2 | 11/2003 | Sandewicz et al. | 424/195.15 |
| 6,979,469 B2 | 12/2005 | Ferrari et al. | 424/707 |
| 7,160,550 B2 | 1/2007 | Brieva et al. | 424/401 |
| 7,199,456 B2 | 4/2007 | Krappe et al. | 257/679 |
| 7,253,249 B2 | 8/2007 | Pavlin | 528/272 |
| 7,297,678 B2 | 11/2007 | Kumar et al. | 514/2 |
| 7,365,014 B2 | 4/2008 | Bencher et al. | 438/700 |
| 2002/0119109 A1 | 8/2002 | Herpens et al. | 424/68 |
| 2004/0141938 A1 | 7/2004 | Gallinat et al. | 424/70.14 |
| 2004/0180027 A1 | 9/2004 | Kumar et al. | 424/70.14 |
| 2004/0258721 A1 | 12/2004 | Bauer et al. | 424/401 |
| 2005/0201961 A1 | 9/2005 | Lu et al. | 424/63 |
| 2005/0244351 A1 | 11/2005 | Reinhart et al. | 424/63 |
| 2005/0287102 A1 | 12/2005 | Ferrari et al. | 424/70.17 |
| 2006/0088562 A1 | 4/2006 | Brieva et al. | 424/401 |
| 2006/0110345 A1 | 5/2006 | Lu et al. | 424/64 |
| 2006/0216318 A1 | 9/2006 | Majmudar | 424/401 |
| 2006/0246027 A1 | 11/2006 | Tanner | 424/70.12 |
| 2006/0292096 A1 | 12/2006 | Yu | 424/64 |
| 2007/0093619 A1 | 4/2007 | Bui et al. | 525/477 |

FOREIGN PATENT DOCUMENTS

DE 10 2005 057593 1/2007
WO WO 2009/059869 5/2009

OTHER PUBLICATIONS

"Dow Corning aerogels provide soft-focus effect," Household & Personal Products Industry, vol. 44, p. 99, Apr. 1, 2007.
"Making light of wrinkles," Cosmetics International, vol. 31, p. 15, Mar. 23, 2007.
"Seen at 'In-Cosmetics' Barcelona," Parfums Cosmetiques Actualities, vol. 189, Jun. 1, 2006.
PCT International Preliminary Report on Patentability issued in International application No. PCT/US09/37822, dated Feb. 15, 2011.
International Search Report and Written Opinion, issued in Application No. PCT/US2009/037822, date of mailing Jul. 16, 2009.

*Primary Examiner* — Jennifer M Kim

(74) *Attorney, Agent, or Firm* — Fulbright & Jaworski L.L.P.

(57) ABSTRACT

Sebum absorption compositions are disclosed which include (a) 1% to 20% by weight of the composition of a sebum absorption ingredient; and (b) 20% to 99% by weight of the composition of a volatile solvent.

3 Claims, 2 Drawing Sheets

SEBUM ABSORPTION COMPOSITIONS

CROSS REFERENCE TO RELATED APPLICATIONS

This application claims the benefit of U.S. Provisional Application No. 61/039,337, filed 25 Mar. 2008. The entire contents of this application are incorporated by reference.

BACKGROUND OF THE INVENTION

A. Field of the Invention

The present invention relates generally to topical skin compositions that can be used to reduce the appearance of shiny or oily skin or that can be used to increase the wearability of cosmetic compositions.

B. Description of Related Art

Human skin naturally manufactures and secrets an oily substance called sebum from sebaceous glands located near the skin surface. Sebum lubricates and protects skin against moisture loss by forming a film over the surface of the skin. A build-up of sebum on the surface of skin can cause the skin to appear shiny or oily. Besides the visually unappealing appearance of shiny or oily skin, sebum build-up can also highlight skin imperfections, promote skin acne development, and reduce the wearability of cosmetic compositions such as foundations.

Current methods that are used to reduce the amount of sebum on the surface of skin include increasing the consumption of water, applying moisturizers to skin, and using compositions that attempt to absorb sebum from skin. Problems associated with current sebum absorption compositions is that the absorbing ingredient(s) tends to coalesce together which causes the composition to cake or streak on the skin surface.

SUMMARY OF THE INVENTION

One aspect of the present invention concerns a composition that can provide sebum absorption from the skin while avoiding the unsightly caking or streaking that has been seen in previous sebum absorption compositions. One of the aspects of the composition is that the composition can include only two ingredients (although several others can be added as explained throughout the specification). In particular embodiments, the concentration ranges of the ingredients can play a role in preparing a sebum absorption composition that is tailored to particular skin types (e.g., oily skin, normal skin, normal to oily skin, normal to dry skin, dry skin, etc.).

In one embodiment of the present invention, there is disclosed a sebum absorption composition that includes 1% to 20% by weight of the composition of a sebum absorption ingredient; and 20% to 99% by weight of the composition of a volatile solvent. Other concentration ranges are contemplated through this specification. For example, the sebum absorption ingredient, can be present in an amount of 0.1, 0.5, 1, 2, 3, 4, 5, 6, 7, 8, 9, 10, 11, 12, 13, 14, 15, 16, 17, 18, 19, 20, 25, 30, 40, 50, 60, 70% or more, or any range or integer therein, based on the total weight of the composition. Similarly, the volatile solvent can be present in a variety of amounts, including 10, 15, 20, 25, 30, 35, 40, 45, 50, 55, 60, 65, 70, 75, 80, 81, 82, 83, 84, 85, 86, 87, 88, 89, 90, 91, 92, 93, 94, 95, 96, 97, 98, or 99%, or any range or integer therein, based on the total weight of the composition. In certain aspects, the composition consisting essentially of 1% to 20% by weight of the composition of the sebum absorption ingredient and 20% to 99% by weight of the composition of the volatile solvent. The composition can be completely made up of a sebum absorption ingredient and a volatile solvent (e.g., a sebum absorption composition consisting of 1% to 20% by weight of the composition of the sebum absorption ingredient and 20% to 99% by weight of the composition of the volatile solvent). In particular embodiments, the sebum absorption ingredient is a silica containing compound. Non-limiting examples of silica containing compounds include silica silylate, silca dimethicone silylate, silica dimethyl silylate, or a combination thereof. The combination can be made up of two or all three of silica silylate, silca dimethicone silylate, and silica dimethyl silylate. Volatile solvents that can be used in the context of the present invention are also described throughout this specification and incorporated by reference. Non-limiting examples of volatile solvents include cyclopentasiloxane, cyclotetrasiloxane, cyclohexasiloxane, isododecane, ethanol, volatile dimethicones, and volatile straight or branched chain hydrocarbons. In particular aspects of the present invention, the compositions can be oil-free, substantially anhydrous, and/or anhydrous.

It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc. as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

Also disclosed are a variety of methods in which the compositions of the present invention described above and throughout this specification can be used. For instance, one method includes reducing the appearance of shiny or oily skin comprising topically applying a sebum absorption composition of the present invention to skin, wherein topical application of the composition to skin reduces the appearance of shiny or oil skin. Another method includes removing sebum from the surface of skin comprising topically applying a sebum absorption composition of the present invention to skin, wherein topical application of the sebum absorption composition to skin removes sebum from the surface of skin. In certain aspects, the composition can remove or absorb sebum from the surface of the skin for a particular period of time (non-limiting examples of a period of time range from 1, 5, 10, 15, 20, 30, 40, 50, 60 minutes or more, 1, 2, 3, 4, 5, 6, 7, 8, 9, 10, 11, 12, 13, 14, 15, 16, 17, 18, 19, 20, 21, 22, 23, 24 hours or more, 1, 2, 3, 4, 5, 6, 7 days or more). In particular embodiments, the composition can reduce the amount of sebum on the surface of the skin by at least 50%, 51%, 52%, 53%, 54%, 55%, 56%, 57%, or more over a 10 hour period when compared with the amount of sebum on the surface of the skin where the composition has not been applied to skin. In other embodiments, the composition can reduce the amount of sebum on the surface of the skin by at least 50%, 51%, 52%, 53%, 54%, 55%, 56%, 57%, 58%, 59%, 60%, 61%, 62%, 63%, 64%, 65% or more over an 8 hour period when compared with the amount of sebum on the surface of the skin where the composition has not been applied to skin. In yet another embodiment, the composition can reduce the amount of sebum on the surface of the skin by at least 50%, 51%, 52%, 53%, 54%, 55%, 56%, 57%, 58%, 59%, 60%, 61%, 62%, 63%, 64%, 65%, 66%, 67%, 68% or more over a 6 hour period when compared with the amount of sebum on the surface of the skin where the composition has not been applied to skin. Non-limiting examples of how to determine the amount of sebum on a person's skin are known in the art and disclosed throughout this specification (e.g., a Courage & Khazaka Sebumeter SM 810 can be used). Also disclosed is a method for increasing the period of time that a cosmetic composition can be worn on skin without losing its aesthetic appearance comprising applying a sebum absorption composition of the present invention to skin and applying a cosmetic composition onto the sebum absorption composition, wherein the cosmetic composition retains its aesthetic appearance for a longer period of time when compared to the same cosmetic composition that has been applied directly to the surface of skin. Non-limiting examples of cosmetic formulations that can benefit from the sebum absorption compositions disclosed by the inventor include lipstick, foundation, face powder, blush, eye shadow, or film formers (e.g., film formers such as acrylate polymers and silicone acrylate (acrylates/polytrimethylsiloxymethacrylate copolymer)). Another method contemplated includes a method for increasing the period of time that a cosmetic composition can be worn on skin and maintain its functionality comprising applying a sebum absorption composition of the present invention to skin and applying a cosmetic composition onto the sebum absorption composition, wherein the cosmetic composition retains its functionality for a longer period of time when compared to the same cosmetic composition that has been applied directly to the surface of skin. A further method includes increasing the period of time that a cosmetic composition can be worn on skin without breaking down comprising applying a sebum absorption composition of the present invention to skin and applying a cosmetic composition onto the sebum absorption composition, wherein the cosmetic composition can be worn on skin without breaking down for a longer period of time when compared to the same cosmetic composition that has been applied directly to the surface of skin. Also contemplated is a method for treating or preventing skin acne, comprising topically applying a sebum absorption composition of the present invention to skin, wherein topical application of the sebum absorption composition to skin removes sebum from the surface of skin and treats or prevents skin acne. Additionally, there is disclosed a method for cosmetically improving the appearance of skin imperfections, comprising topically applying a sebum absorption composition of the present invention to skin, wherein topical application of the sebum absorption composition to skin improves the appearance of skin imperfections. Non-limiting examples of skin imperfections are fine lines, wrinkles, or skin blemishes caused by acne, sun exposure, age, spots, sores, etc.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of example embodiments presented here. The drawings are examples only and do not limit the claims.

DESCRIPTION OF ILLUSTRATIVE EMBODIMENTS

Figure 1:
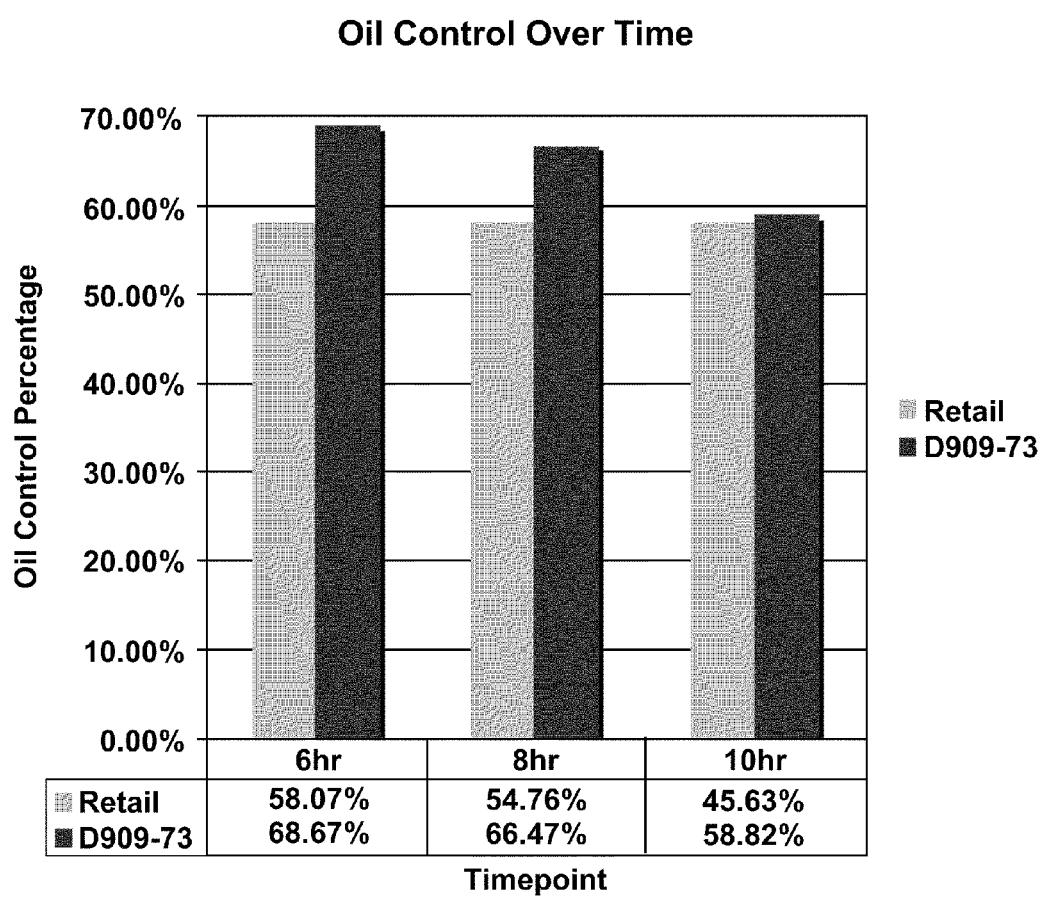
FIG. 1 concerns data showing the efficacy of a non-limiting sebum control composition (D909-73) of the present invention.

In today's image conscious society, people are continually looking for a product that can improve the visual appearance of their skin. Often times, skin overproduces sebum which can cause skin to appear oily or shiny and have a slippery feel. The build-up of sebum can also result from normally functioning sebaceous glands in instances where the skin has not been washed for an extended period of time. Besides the visually unappealing appearance of shiny or oily skin, sebum build-up can also highlight skin imperfections, promote skin acne development, and reduce the wearability of cosmetic compositions such as foundations.

Disclosed is a sebum absorption composition that can absorb or remove sebum from the surface of the skin. As explained in non-limiting aspects in the following sections, the composition can comprise, consist essentially of, or consist of a sebum absorption ingredient and a volatile solvent. The concentration ranges of these ingredients can be varied to particular skin types (e.g., oil skin, dry skin, normal skin, etc.). In this regard, the compositions can be made to a particular skin type. In certain non-limiting embodiments, the composition can include only two ingredients (e.g., sebum absorption ingredient and a volatile solvent) and still be effective in removing or absorbing sebum from the surface of the skin, while also maintaining pharmaceutically and/or cosmetically elegant properties. This has the particular advantage of reducing the costs associated with obtaining the ingredients and preparing such a composition (i.e., only two ingredients can be used to achieve a desired result). These and other aspect of the present invention are described in further non-limiting detail below.

A. Sebum Absorption Ingredients

Sebum absorption ingredients have the capability of absorbing or removing sebum from the surface of the skin. Examples of such ingredients include silica containing compounds. Silica is a silicone dioxide that can be modified by the addition of various chemical groups to the Si portion of silicone dioxide. Examples of Silica containing ingredients include silica silylate, silica dimethyl silylate, and silica dimethicone silylate.

Silica silylate is a hydrophobic silica derivative where some of the hydroxyl groups on the surface of the fumed silica have been replaced by trimethylsiloxyl groups. This ingredient can be purchased under the Tradenames VM-2270 (Dow Corning, United States), Aerosil R 812 (Deggussa AG, Germany), Aerosil RX 300 (Degussa AG, Germany), Sipernat D 17 (Degussa AG, Germany), CAB-O-SIL TS-530 (Cabot, United States), Wacker HDK H2000 (Wacker-Chemie AG, Germany).

Another example of a sebum absorption ingredient that can be used in the context of the present invention includes silica dimethyl silylate. This ingredient is a silica derivative in which the surface of the fumed silica has been modified by the addition of dimethyl silyl groups. Silica dimethyl silylate can be purchased under the Tradenames Aerosil R 972 (Degussa AG, Germany), Aerosil R 974 (Degussa AG, Germany), Aerosil R 976 (Degussa AG, Germany), Aerosil R 976 S (Degussa AG, Germany), CAB-O-SIL TS-610 (Cabot, United States), Covasilic 15 (Sensient Cosmetic Technologies-LCW, France), Wacker HDK H15 (Wacker-Chemie, Germany), Wacker HDK H18 (Wacker-Chemie, Germany), and Wacker HDK H20 (Wacker-Chemie, Germany).

A further example of a sebum absorption ingredient that can be used in the context of the present invention includes silica dimethicone silylate. This ingredient is a hydrophobic silica derivative in which the surface of the fumed silica has been modified by the addition of dimethicone. Silica dimethicone silylate can be purchased under the Tradename CAB-O-SIL TS-720 (Cabot, United States).

B. Volatile Solvents

A wide variety of volatile solvents can be used in the context of the present invention. Non-limiting examples can be found in The CTFA International Cosmetic Ingredient Dictionary and Handbook (2004 and 2008 versions), U.S. Pat. No. 6,645,502, U.S. Pat. No. 6,444,212, and U.S. Publication 2005/0244351, all of which are incorporated by reference. In general, a volatile solvents typical include solvents which evaporate easily. Examples include cyclic silicones having the formula:

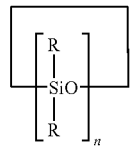

wherein R is individually H or $CH_3$ and n is between 3-7. Examples of volatile linear silicones that can be used include those having the following formula:

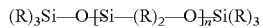

wherein R is individually H or $CH_3$ and n is between 0-7. Examples of volatile solvents include cyclopentacyloxane, cyclotetrasiloxane, cyclohexasiloxane, isododecane, or ethanol.

Other volatile solvents that can be used include various straight or branched chain paraffinic hydrocarbons having about 5 to 40 carbon atoms. Non-limiting examples include pentane, hexane, heptane, decane, dodecane, tetradecane, tridecane, and $C_{8-20}$ isoparaffins (see, e.g., U.S. Pat. Nos. 3,439,088 and 3,818,105, which are incorporated by reference). Another non-limiting class of volatile solvents that can be used include volatile dimethicones (see, e.g., U.S. Pat. No. 6,346,238 and CTFA International Cosmetic Ingredient Dictionary and Handbook (2004 and 2008 versions), which are incorporated by reference).

Volatile solvents can be prepared by using convention chemical synthesis techniques (see, e.g., Organic Chemistry, $5^{th}$ Ed.).

C. Derivatives and Modification of Sebum Absorption Ingredients and Volatile Solvents Derivatives and modifications to the aromatic skin-active ingredients of the present invention are also contemplated in the context of the present invention. Non-limiting examples of modifications that can be made to such ingredients include the addition or removal of lower alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; and substitution of a phenyl by a larger or smaller aromatic group. Alternatively, in a cyclic or bicyclic structure, hetero atoms such as N, S, or O can be substituted into the structure instead of a carbon atom.

D. Compositions of the Present Invention

1. Combinations and Amounts of Ingredients

It is contemplated that the compositions of the present invention can include any number of combinations of the sebum absorption ingredients and volatile solvents. Additionally, the compositions can include any number of combinations of additional ingredients described throughout this specification. The concentrations of the sebum absorption ingredients, volatile solvents, or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the sebum absorption ingredients, volatile solvents, or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Cosmetic Compositions

Cosmetic compositions can be applied onto the compositions of the present invention to preserve the integrity of the cosmetic compositions, increase the wearability of the cosmetic compositions, or to prevent sebum from coming into contact with the cosmetic compositions. Non-limiting examples of such cosmetic compositions include sunscreen products, sunless skin tanning products, hair products, fingernail products, moisturizing creams, skin benefit creams and lotions, softeners, day lotions, gels, ointments, foundations, night creams, lipsticks, mascaras, eyeshadows, eyeliners, cheek colors, cleansers, toners, masks, or other known cosmetic products or applications.

3. Additional Ingredients

Compositions of the present invention can include additional cosmetic ingredients. The CTFA International Cosmetic Ingredient Dictionary and Handbook (2004 and 2008 versions) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, avobenzone, octocrylene, oxybenzone, homosalate, octinocate, octisalate, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), and thickening agents (e.g., substances which that can increase the viscosity of a composition such as carboxylic acid polymers, crosslinked polyacrylate polymers, polyacrylamide polymers, polysaccharides, and gums).

E. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Non-Limiting Sebum Absorption Composition

Table 1 includes a non-limiting sebum absorption composition of the present invention:

TABLE 1*

| Phase | Ingredient | % (in grams) |
| --- | --- | --- |
| A | Cyclopentasiloxane | 93.00 |
| B | Silica Silylate | 7.00 |
| TOTAL | | 100.00 |

*The Composition was prepared as follows: Mix phase A in container. Add phase B and continued mixing until powder dispersed throughout mixture. Visually inspected mixture to ensure that no small powder pockets were present. Mixture thickens to form a gel.

Example 2

Sebum Absorption Data

Overview of Study: A study was conducted to determine the efficacy of the Composition in Table 1. This study included comparing the sebum absorption capabilities of the Composition over a ten (10) hour period with a currently sold sebum control composition (i.e., Mary Kay Oil Mattifier or "Retail Product", which can be purchased from Mary Kay (Dallas, Tex.)). The Retail Product includes the following ingredients:

Water, Isododecane, Cyclopentsiloxane, Butylene Glycol, Silica, Alcohol Denat., Methyl Mthacrylate Crosspolymer, Cetyl Dimethicone Copolyol, Cyclohexasiloxane, Dimethicone, Aluminum Startch Octenylsuccinate, Dimethicone Crosspolymer, Quaternium-18 Bentonite, Willow Bark Extract, Ethylene/Acrylic Acid Copolymer, Propylene Glycol, Trimethylsiloxysilicate, Sodium Chloride, Sorbitan Sesquioleate, Propylene Carbonate, Diazolidinyl Urea, Methylparaben, and Propylparaben.

Study Protocol: Six (6) panelists (humans) participated on this study. The panelists were instructed not to apply any products on their forehead on the morning of the test. Each panelist's forehead was divided into three sections. Baseline measurements of each section were taken with the Courage & Khazaka Sebumeter SM 810. A cosmetically acceptable amount of test product (Composition of Table 1 and Retail Product) was applied to two out of the three sections and rubbed in by the study investigator with a sponge. Panelists returned to the SCR facility 6, 8 and 10 hours later, where Sebumeter measurements were repeated. Data was analyzed for statistical significance with an ANOVA and t-test.

Results: As shown in FIG. 1. and Table 2, the current Retail Product controlled sebum for 10 hours, with a 58.07%, 54.76% and 45.63% reduction in sebum from the untreated site at 6, 8 and 10 hours respectively. By comparison, the sebum control Composition in Table 1 (D909-73 of FIG. 1) controlled sebum for 10 hours, with a 68.67%, 66.47% and 58.82% reduction in sebum from the untreated site at 6, 8 and 10 hours respectively.

TABLE 2*

| (Reduction in Sebum from Untreated Site) | | | |
| --- | --- | --- | --- |
| Composition | 6 hr | 8 hr | 10 hr |
| Table 1 | 68.67% | 66.47% | 58.82% |
| Retail Product | 58.07% | 54.76% | 45.63% |

*All percentages are statistically significant from the untreated site at ≧95% confidence level.

Example 3

Non-Limiting Second Sebum Absorption Composition

Table 3 includes a non-limiting second sebum absorption composition of the present invention:

TABLE 3*

| Phase | Ingredient | % (in grams) |
| --- | --- | --- |
| A | Cyclopentasiloxane | 73.00 |
| | Dimethicone | 20.00 |
| B | Silica Silylate | 7.00 |
| TOTAL | | 100.00 |

*The Composition was prepared as follows: Mix phase A in container. Add phase B and continued mixing until powder dispersed throughout mixture. Visually inspected mixture to ensure that no small powder pockets were present. Mixture thickens to form a gel.

Example 4

Shine Control Data

Overview of Study: A study was conducted to determine the efficacy of the Composition in Table 3 to control the appearance of shiny skin over a six (6) our period.

Study Protocol: Nineteen (19) adults were enrolled and completed the study. Panelists were asked to not apply any product, other than the test formulation illustrated in Table 3, to the forehead for the duration of the study. Panelists washed their face with the provided cleanser prior to having any measurements taken. A baseline shine reading of the forehead was taken at the initial visit. Panelists then applied the test product to the entire face. A second shine reading was taken immediately after product application. A final shine reading was taken 6 hours after product application. Each panelist was also given a questionnaire regarding their perception of shine at the baseline and 6 hour evaluations. The baseline, immediate, and 6 hour measurements were taken using the Konica Minolta Glossmeter (per Biophysical SOP 005).

Figure 2:
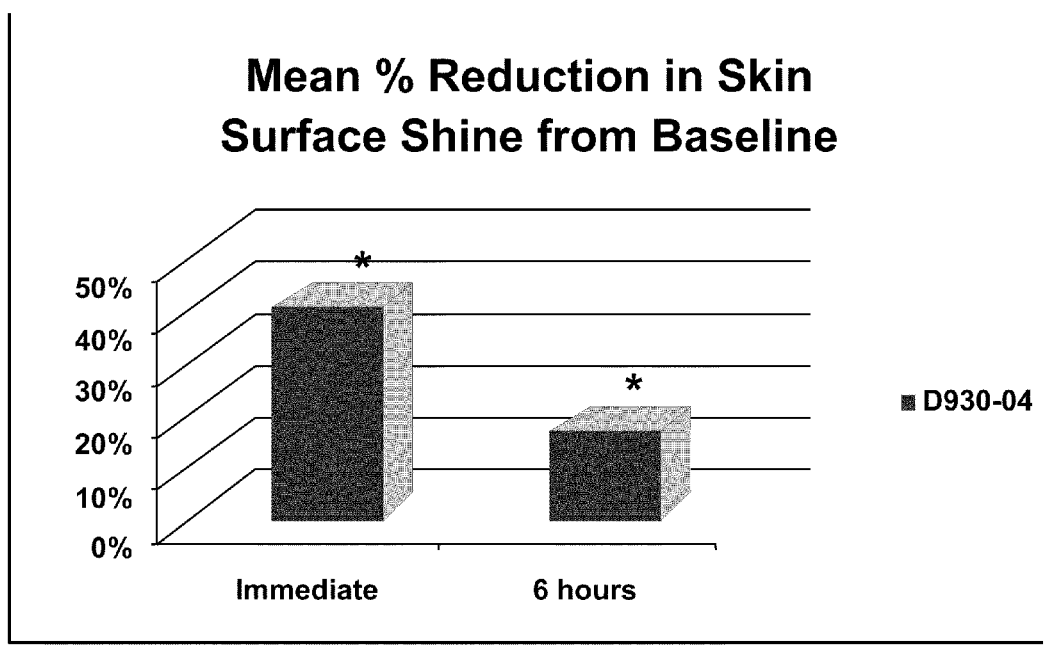
FIG. 2 concerns data showing the efficacy of a non-limiting sebum control composition (D930-04) of the present invention.

Results: The mean % reduction in skin surface shine from the baseline measurement was 41% after immediate application and 17% after six (6) hours from application of the test formulation illustrated in Table 3 (note: statistically significant at $\geq$95% confidence level. The Results are also illustrated in FIG. 2 (note: D930-04 is the Table 3 formulation). These data illustrate that the Table 3 formulation significantly reduced shine on the skin at the immediate and six (6) hour readings.

All of the compositions or methods disclosed and claimed in this specification can be made and executed without undue experimentation in light of the present disclosure. While the compositions or methods of this invention have been described in terms of particular embodiments, it will be apparent to those of skill in the art that variations may be applied to the compositions or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.

U.S. Pat. No. 3,439,088
U.S. Pat. No. 3,818,105
U.S. Pat. No. 6,346,238
U.S. Pat. No. 6,444,212
U.S. Pat. No. 6,645,502
U.S. Publn. 2005/0244351
Organic Chemistry, $5^{th}$ Ed.
The CTFA International Cosmetic Ingredient Dictionary and Handbook, 2004 $10^{th}$ edition.
The CTFA International Cosmetic Ingredient Dictionary and Handbook, 2008, $12^{th}$ edition.

The invention claimed is:

1. A method for removing sebum from the surface of skin in a human in need thereof comprising topically applying to the skin a composition consisting of:
   (a) at least 5% by weight of the composition of a silica silyate;
   (b) at least 70% by weight of the composition of cyclopentasiloxane; and
   (c) at least 15% by weight of dimethicone,
   wherein topical application of the sebum absorption composition to the skin removes sebum from the surface of the skin.

2. The method of claim 1, wherein the composition is applied to oily skin or skin having a shiny appearance.

3. The method of claim 1, wherein the composition reduces the amount of sebum on the surface of skin by at least 60% over a six hour period when compared with the amount of sebum on the surface of the skin where the composition has not been applied.

* * * * *